United States Patent
Tadepalli et al.

(10) Patent No.: US 11,753,360 B2
(45) Date of Patent: Sep. 12, 2023

(54) CIRCULAR ECONOMY METHODS OF PREPARING UNSATURATED COMPOUNDS

(71) Applicant: INTERNATIONAL FLAVORS & FRAGRANCES INC., New York, NY (US)

(72) Inventors: Sunitha Rao Tadepalli, Morganville, NJ (US); Geatesh Karunakaran Tampy, Colts Neck, NJ (US); Anubhav P. S. Narula, Hazlet, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 16/556,963

(22) Filed: Aug. 30, 2019

(65) Prior Publication Data

US 2019/0389791 A1    Dec. 26, 2019

Related U.S. Application Data

(62) Division of application No. 15/624,749, filed on Jun. 16, 2017, now Pat. No. 10,435,345.

(60) Provisional application No. 62/351,062, filed on Jun. 16, 2016.

(51) Int. Cl.
| | |
|---|---|
| *C07B 35/04* | (2006.01) |
| *C07C 45/66* | (2006.01) |
| *C07C 5/10* | (2006.01) |
| *C07C 5/333* | (2006.01) |
| *C07C 5/48* | (2006.01) |
| *C07C 45/65* | (2006.01) |
| *C07C 67/317* | (2006.01) |
| *C07C 5/367* | (2006.01) |
| *C07D 307/79* | (2006.01) |

(52) U.S. Cl.
CPC .............. *C07C 45/66* (2013.01); *C07B 35/04* (2013.01); *C07C 5/10* (2013.01); *C07C 5/333* (2013.01); *C07C 5/3332* (2013.01); *C07C 5/3337* (2013.01); *C07C 5/367* (2013.01); *C07C 5/48* (2013.01); *C07C 45/65* (2013.01); *C07C 67/317* (2013.01); *C07D 307/79* (2013.01); *C07C 2521/08* (2013.01); *C07C 2521/18* (2013.01); *C07C 2523/22* (2013.01); *C07C 2523/28* (2013.01); *C07C 2523/44* (2013.01); *C07C 2523/50* (2013.01); *C07C 2523/62* (2013.01); *C07C 2523/66* (2013.01); *C07C 2523/89* (2013.01); *C07C 2527/198* (2013.01); *C07C 2531/24* (2013.01); *C07C 2601/18* (2017.05); *C07C 2602/08* (2017.05); *C07C 2602/24* (2017.05); *C07C 2602/28* (2017.05)

(58) Field of Classification Search
CPC .................................................... C07B 35/04
See application file for complete search history.

(56) References Cited

U.S. PATENT DOCUMENTS

| | | | | |
|---|---|---|---|---|
| 3,751,500 | A * | 8/1973 | Hall ..................... | C11B 9/0049 |
| | | | | 585/22 |
| 3,847,993 | A | 11/1974 | Hall et al. ..................... | 568/360 |
| 10,435,345 | B2 * | 10/2019 | Tadepalli .................. | C07C 5/10 |
| 11,021,421 | B2 * | 6/2021 | Tadepalli .................. | C07C 5/50 |
| 2015/0251171 | A1 | 9/2015 | Kumar et al. ................ | 585/656 |
| 2018/0362420 | A1 * | 12/2018 | Tadepalli ............... | C07C 13/48 |

FOREIGN PATENT DOCUMENTS

| | | | |
|---|---|---|---|
| CN | 1117037 | 2/1996 | |
| WO | WO 2005/073157 | 8/2005 | |
| WO | WO-2018001963 A1 * | 1/2018 | ............. B01J 23/44 |

OTHER PUBLICATIONS

"Hydrogen Acceptor." The Free Dictionary.com. Accessed Aug. 14, 2020. (Sep. 19, 2011). Available from: < https://medical-dictionary.thefreedictionary.com/hydrogen+acceptor >. (Year: 2011).*

Jiang, N., et al. "Effect of hydrogen spillover in decalin dehydrogenation over supported Pt catalysts." Applied Catalysis A: General. (2012), vol. 425-426, pp. 62-67. (Year: 2012).*

Igarashi, M., et al. "Transition Metal-Catalyzed Dehydrogenative Silylation of Ketones with Amine and Halide as Cocatalysts." Tetrahedron Letters. (1999), vol. 40, pp. 711-714. (Year: 1999).*

ThalesNano. "About Flow Chemistry." Accessed Aug. 14, 2020. (Dec. 1, 2013). Available from: < https://thalesnano.com/applications/about-flow-chemistry/ >. (Year: 2013).*

"Packed Bed Reactors." Visual Encyclopedia of Chemical Engineering. Accessed Aug. 14, 2020. (Feb. 16, 2012). Available from: < http://encyclopedia.che.engin.umich.edu/Pages/Reactors/PBR/PBR.html >. (Year: 2012).*

Extended European Search Report issued in EP 17176464.0 dated Feb. 20, 2018.

Alyea, E.C. and Keane, M.A. "The oxidative dehydrogenation of cyclohexane and cyclohexene over unsupported and supported molybdena catalysts prepared by metal oxide vapor deposition" Journal of Catalysts 1996 164:28-35.

Findlater et al. "Chapter 4 Alkane dehydrogenation" P.J. Perez (editor), Alkane C—H Activation by Single-Site Metal Catalysis, Catalysis by Metal Complexes 2012 38:113-141.

Fujii et al. "Thermal dehydrogenation of cyclooctane by supported noble metal catalysts" The Chemical Society of Japan 1991 64:938-941.

Furukawa et al. "Catalytic properties of Pt-based intermetallic compounds in dehydrogenation of cyclohexane and n-butane" Applied Catalysis A: General 2014 469:300-305.

Gao et al. "General palladium-catalyzed aerobic dehydrogenation to generate double bonds" Chem. Sci. 2012 3:883-886.

(Continued)

*Primary Examiner* — John S Kenyon

(57) ABSTRACT

Methods of preparing unsaturated compounds or analogs through dehydrogenation of corresponding saturated compounds and/or hydrogenation of aromatic compounds are disclosed.

5 Claims, 1 Drawing Sheet

(56) References Cited

OTHER PUBLICATIONS

Gunanathan, C. and Milstein, D. "Bond activation and catalysis by ruthenium pincer complexes" Chem. Rev. 2014 114:12024-12087.

Gupta et al. "Catalytic dehydrogenation of cycloalkanes to arenes by a dihydrido iridium P-C-P pincer complex" J. Am. Chem. Soc. 1997 119:840-841.

Jensen, C. M. "Iridium PCP pincer complexes: highly active and robust catalysts for novel homogenous aliphatic dehydrogenations" Chem. Commun. 1999 2443-2449.

Kung, M.C. and Kung, H.H. "Oxidative dehydrogenation of cyclohexane over vanadate catalysts" Journal of Catalysis 1991 128:287-291.

Liu et al. "Direct oxidation of β-Aryl substituted aldehydes to α,β-unsaturated aldehydes promoted by an o-Anisidine-Pd(OAc)$_2$ co-catalyst" Chem. Asian J. 2009 4:1712-1716.

Mahdavi, V. and Hasheminasab, H. R. "Liquid-phase efficient oxidation of cyclohexane over cobalt promoted VPO catalyst using tert-butylhydroperoxide" Journal of the Taiwan Institute of Chemical Engineers 2015 1-10.

Ninomiya et al. "Dehydrogenation of cycloaklanes over noble metal catalysts supported on active carbon" Res. Chem. Intermed. 2008 34:663-668.

Pande et al. "Catalytic dehydrogenation of cyclohexane over Ag-M/ACC catalysts for hydrogen supply" International Journal of Hydrogen Energy 2012 37:6756-6763.

Shvo, Y. and Arisha, A. H. "Regioselective catalytic dehydrogenation of aldehydes and ketones" J. Org. Chem. 1998 63:5640-5642.

Zhu et al. "A direct amine-palladium acetate cocatalyzed saegusa oxidation reaction of unmodified aldehydes to α,β-unsaturated aldehydes" Adv. Synth. Catal. 2009 351:1229-1232.

\* cited by examiner

PROCESS SCHEME FOR THPMI PRODUCTION FROM PMI
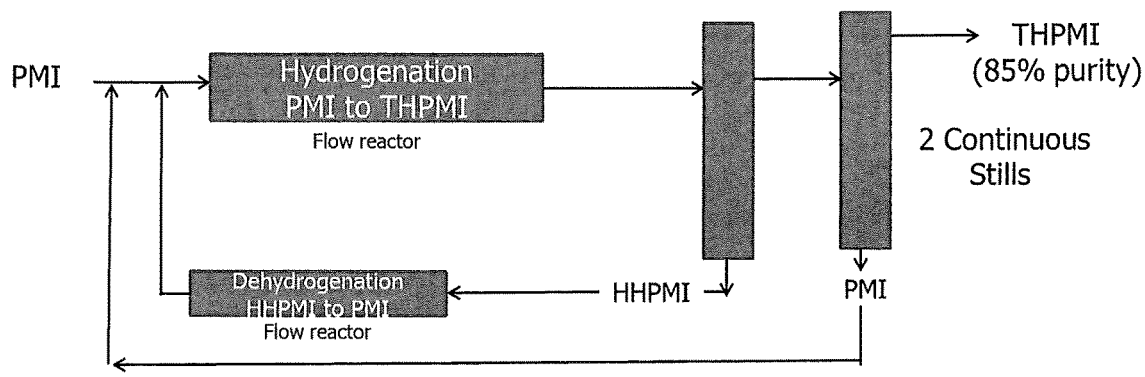

CIRCULAR ECONOMY METHODS OF PREPARING UNSATURATED COMPOUNDS

INTRODUCTION

This application is a divisional of U.S. Ser. No. 15/624,749 filed Jun. 16, 2017, which claims priority to U.S. Application, Ser. No. 62/351,062, filed on Jun. 16, 2016, the contents of which are incorporated herein by reference in their entirety.

FIELD OF THE INVENTION

This application relates to methods of preparing unsaturated compounds, especially unsaturated carbocyclic compounds useful in the fragrance industry, through hydrogenation of aromatic compounds or dehydrogenation of saturated compounds using sustainable, green engineering and circular economy methods.

BACKGROUND OF THE INVENTION

Olefins (alkenes) are versatile raw materials in organic synthesis, polymerization, and chemical processes, but they are not as widely available naturally as alkanes. Given the abundance of saturated hydrocarbon or alkanes in nature, dehydrogenation of alkanes provides a sustainable production of alkenes. This approach eliminates significant amount of waste generated from alternate multi-step chemical methods that are used to produce these olefins.

Different dehydrogenation methods have been developed. Traditional methods involve use of stoichiometric amounts of halogenated reagents and/or precious metals thus generating a lot of waste. Alternate one-step catalytic methods have been developed, but productivity and selectivity remains to be an issue especially when multiple regio-isomers can be formed in the dehydrogenation process. Especially in the case of higher alkanes, low selectivity and conversion often severely limit the utility of dehydrogenation.

Accordingly, there remains a need for green dehydrogenation methods that can produce high yield and great selectivity via engineering and catalytic methods. In one aspect, the present disclosure provides inventions aiming to meet such needs.

SUMMARY OF THE INVENTION

Many fragrance intermediates and ingredients contain unsaturated backbones—linear or branched chain, mono- or multi-cyclic carbon backbones with or without functional groups. Dehydrogenation from the corresponding saturated compounds to yield these unsaturated compounds often encounters low-selectivity issues, giving rise to different regio-isomers of olefins or the aromatic counterparts. To access some of the unsaturated carbocyclic compounds, an alternative approach is through hydrogenation of the corresponding aromatic carbocycles, but control of hydrogenation at the olefin stage to avoid complete hydrogenation to fully saturated carbocyclic compounds remains a challenge. It has been unexpectedly discovered that various new catalytic systems and engineering methods are efficient to tackle this challenge.

In one aspect, the present invention provides methods of preparing unsaturated compounds, especially those comprising fragrance carbocyclic compound backbones, through dehydrogenation of corresponding saturated compounds, wherein said fragrance compound backbones contain one or more carbon-carbon double bonds.

In another aspect, the present invention provides methods of preparing unsaturated compounds, especially those comprising fragrance compound backbones, through hydrogenation of corresponding aromatic carbocyclic compounds, wherein said fragrance compound backbones contain one or more carbon-carbon double bonds.

In one embodiment, the present invention provides a method of preparing 1,1,2,3,3-pentamethyl-4,5,6,7-tetrahydro-1H-indene (THPMI) comprising selective hydrogenation of 1,1,2,3,3-pentamethylindane (PMI).

In a preferred embodiment, the method comprises a combination of flow hydrogenation and dehydrogenation processes.

In a particularly preferred embodiment, the present invention provides a method of preparing THPMI comprising selective hydrogenation of PMI or selective dehydrogenation of 1,1,2,3,3-pentamethyloctahydro-1H-indene (HHPMI) in combination with continuous separation of the starting materials, products, or by-products.

Also within the scope of this invention is a process of preparing indomuscone comprising the steps of: (a) feeding PMI into a first reactor having a first catalyst; (b) hydrogenating PMI in the first reactor to obtain a hydrogenation mixture containing THPMI as the desired product, HHPMI as a by-product, and unreacted PMI; (c) feeding the hydrogenation mixture into a second reactor having a second catalyst to oxidize THPMI to indomuscone (i.e., Cashmeran), thereby obtaining an oxidation mixture that contains indomuscone, HHPMI, and PMI; (d) separating indomuscone from HHPMI and PMI to obtain an oxidization side stream containing HHPMI and an oxidization product stream containing indomuscone; (e) feeding the oxidation side stream into a third reactor having a third catalyst to dehydrogenate HHPMI to PMI to obtain a dehydrogenation stream; (f) feeding the dehydrogenation stream into the first reactor to hydrogenate PMI to THPMI; and (g) collecting indomuscone in the oxidization product stream. The process can further comprise the steps of: (d1) separating PMI from the oxidization side stream to obtain a PMI oxidization stream consisting essentially of PMI; and (d2) feeding the PMI oxidization stream into the first reactor to hydrogenating PMI to THPMI. Each of the first, second, and third reactors is either a batch reactor or a flow reactor. When a flow reactor is used, the catalyst contained therein is preferably a fixed-bed catalyst.

Still within the scope of this invention is a process of preparing THPMI comprising the steps of: (a) feeding PMI into a first reactor having a first catalyst; (b) hydrogenating PMI to THPMI in the first reactor to obtain a hydrogenation mixture containing THPMI as the desired product, HHPMI as a by-product, and unreacted PMI; (c) separating HHPMI from the hydrogenation mixture in a first separation column to obtain a first hydrogenation side stream containing HHPMI and a main hydrogenation stream containing THPMI and PMI; (d) passing the first hydrogenation side stream into a second reactor having a second catalyst; (e) dehydrogenating HHPMI in the first hydrogenation side stream to PMI in the second reactor to obtain a dehydrogenation stream; (f) feeding the dehydrogenation stream into the first reactor; (g) separating THPMI in the main stream from PMI in a second separation column to obtain a second hydrogenation stream containing PMI and a hydrogenation product stream containing THPMI; (h) feeding the second hydrogenation side stream into the first reactor; and (i) collecting THPMI in the hydrogenation product stream.

Each of the first and second reactors, independently, is either a batch reactor or a flow reactor. In one embodiment, each of the first and second reactors is a flow reactor, and each of the first and second catalysts, having a particle size of 300 microns or greater, is a fixed-bed catalyst.

In some embodiments, the hydrogenating step (b) is performed using any of the hydrogenation methods described herein, and/or the dehydrogenating step (e) is performed using any of the dehydrogenation methods described herein.

The term "unsaturated compound" refers to an aromatic compound or an aliphatic hydrocarbon having one or more carbon-carbon double bonds (C=C). The aliphatic hydrocarbon can be a cyclic (carbocyclic) compound or straight or branched open chain without a ring. The term "corresponding saturated compound" refers to a compound having a hydrocarbon backbone the same as the unsaturated compound but having no carbon-carbon double bond.

The term "fixed-bed catalyst" refers a catalyst, typically in pellet or granule form, packed in a static bed that allows a gas or liquid to pass through.

The term "flow reactor" refers to a reactor wherein reactants are continuously fed into the reactor and emerge as continuous stream of product.

The term "batch reactor" refers to a vessel in which reactants

Other aspects or benefits of the present invention will be reflected in the following drawings, detailed description, and claims.

BRIEF DESCRIPTION OF THE FIGURES

FIG. 1 illustrates a process scheme for pentamethyl indane (PMI) to form tetrahydro pentamethyl indane (THPMI) using combination of selective hydrogenation, dehydrogenation and separation in a continuous mode.

DETAILED DESCRIPTION OF THE INVENTION

In one aspect, the present invention provides a method of preparing an unsaturated compound, comprising dehydrogenation of a corresponding saturated compound in the presence of a catalyst system under conditions that effect loss of one or more molecules of hydrogen ($H_2$) per molecule of the saturated compound.

In one embodiment, the conditions include one or more solvents (e.g., acetic acid, toluene, ethyl acetate, DMSO, and DMF), an elevated temperature (e.g., at least 50° C., at least 100° C., 50-800° C., 100-800° C., 100-400° C., and 150-350° C.), and/or a stream of nitrogen to purge liberated hydrogen. In one embodiment, the conditions include one or more hydrogen acceptor (e.g., tertiary butyl ethylene, cyclohexene and other alkenes) to consume the liberated hydrogen.

In one embodiment, the catalyst system is selected from the group consisting of heterogeneous catalyst systems, homogeneous catalyst systems, bi-metallic catalyst systems, and combinations thereof.

In another embodiment, the heterogeneous catalyst system is selected from Pd/C, Pd/Alumina, Pd/CG, Pt/C, Pt/Alumina, Molybdenum Oxide, Vanadium Pentoxide, Rh/Alumina, Ru/$Al_2O_3$, Bismuth Molybdate, and combinations thereof.

In another embodiment, the heterogeneous catalyst system is a bi-metallic catalyst system comprising a metal pair including but not limited to Pt—Sn, Pt—Tl, Pt—Co, and Pd—Ag.

In another embodiment, the homogeneous catalyst system is selected from soluble transition metal salts (e.g., Pd(TFA)$_2$, Pd(OAc)$_2$) with or without ligands, pincer-based catalysts (see J. Am. Chem. Soc. 1997, 119, 840-841, Chem. Commun., 1999, 2443-2449; Alkane Dehydrogenation. In Alkane C—H Activation by Single-Site Metal Catalysis, Pérez, P. J., Ed. Springer: New York, 2012; Vol. 38., Chapter 4; Chem. Rev. 2014, 114, 12024-12087; US20150251171A1), and combinations thereof.

A pincer-based catalyst is a catalyst having a metal (typically a transitional metal such as ruthenium, rhodium, palladium, osmium, iridium, and platinum) and a pincer ligand that binds tightly to three adjacent coplanar sites, usually on a transition metal in a meridional configuration.

Exemplary pincer-based catalysts include iridium complex having the structures described in US 2015/0251171 such as ($^{iPr4}$PCP)Ir($C_2H_4$) and (p-OK-$^{iPr4}$PCP)Ir($C_3H_6$), in which iPr refers to isopropyl groups, PCP is $C_6H_3$ ($CH_2PBut_2$)$_2$-2,6), Ir refers to iridium, $C_2H_4$ is ethylene, and $C_3H_6$ is propylene. The iridium complex is either unsupported or immobilized on a solid support including silica, γ-alumina, florisil, neutral alumina.

In another embodiment, the saturated compound comprises of straight chain or branched alkanes with or without functional groups such as aldehyde, ketone, ester, ethers or in combination thereof, each optionally substituted.

In another embodiment the saturated compound comprises a formula selected from the group consisting of:

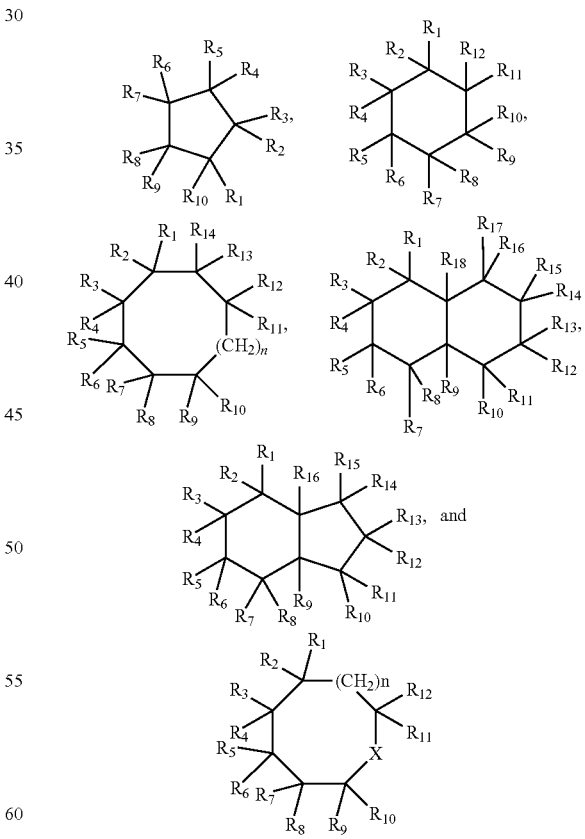

wherein:
n is 0 or an integer selected from 1 to 20; X is a lactone or ether
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$ and $R_{18}$ are each independently H, methyl, ethyl, $C_3$-$C_{10}$ branched, cyclic or straight chain alkyl, ketone, ester, ether, aldehyde, alcohol or vinyl group, or a combination thereof, each optionally substituted; or alternatively, two R groups on the same carbon atom together form an oxo (=O) group.

In another embodiment, the saturated carbocyclic compound comprises a backbone structure selected from the group consisting of:

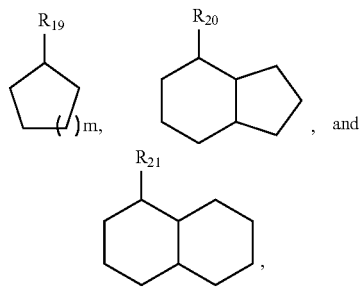

wherein m is an integer from 1 to 20; each of $R_{19}$, $R_{20}$, and $R_{21}$, independently, is hydrogen or oxo (=O), and each open position of said backbone structures is optionally substituted.

In another embodiment, the saturated carbocyclic compound is selected from the group consisting of:

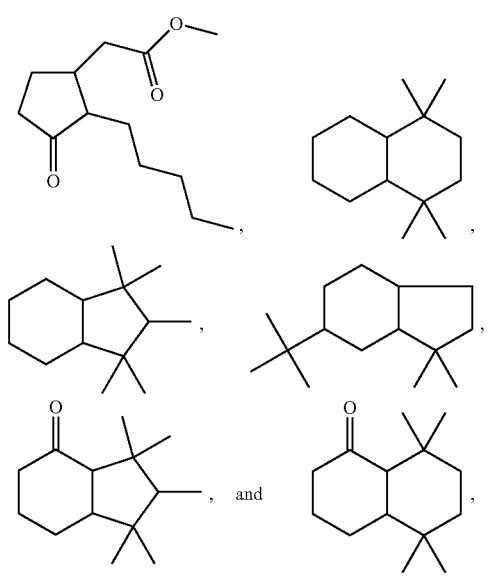

In another embodiment, the present invention provides method of preparing a compound of formula I(a) or I(b), comprising flow dehydrogenation of a compound of formula II (starting material) in the presence of a fixed-bed catalyst:

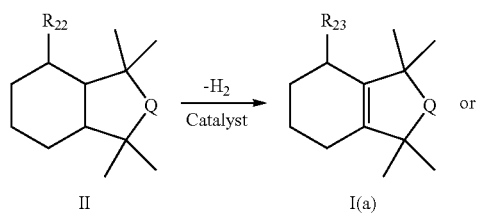

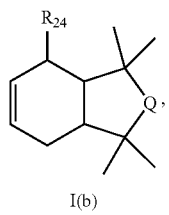

wherein each of $R_{22}$, $R_{23}$, and $R_{24}$, independently, is H or =O; and Q is $CH_2$, $CH_2CH_2$, $CH(CH_3)$, or $C(CH_3)_2$, preferably, Q is $CH_2CH_2$ or $CH(CH_3)$.

In another embodiment, the present invention provides a method of preparing a compound of formula I(a) or I(b). The method comprises selective hydrogenation of a compound of formula III in the presence of a catalyst:

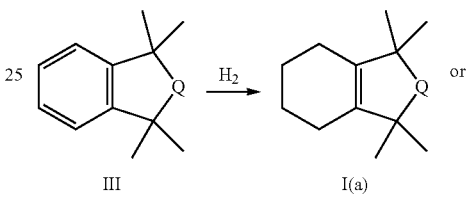

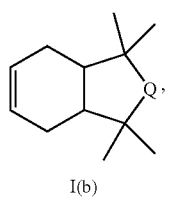

wherein Q is $CH_2$, $CH_2CH_2$, $CH(CH_3)$, or $C(CH_3)_2$.

In another embodiment, the catalyst is a fixed-bed catalyst, and the hydrogenation is conducted in a flow reactor.

In another embodiment, the hydrogenation reaction is combined with dehydrogenation reaction and continuous separation process to separate product from the starting material and by-product.

In another embodiment, the compound of formula (III) is 1,1,2,3,3-pentamethylindane (PMI), and said formula I(a) is 1,1,2,3,3-Pentamethyl-4,5,6,7-tetrahydro-1H-indene (THPMI):

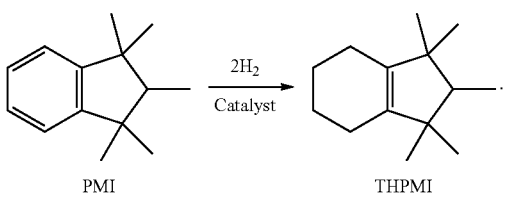

In another embodiment, the present invention provides a method of preparing 1,1,2,3,3-pentamethylindane (PMI), comprising flow dehydrogenation of 1,1,2,3,3-pentamethyl-octahydro-1H-indene (HHPMI) in the presence of a fixed-bed catalyst:

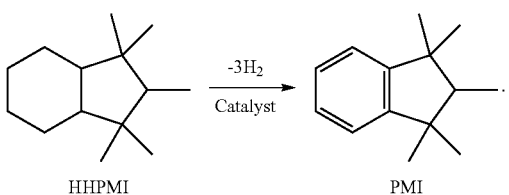

HHPMI → PMI

In another embodiment, the fixed-bed catalyst comprises 5% Pd/C, and the dehydrogenation is conducted in a flow reactor, and a nitrogen stream is passed through the reactor to remove hydrogen molecules formed.

In another embodiment, the dehydrogenation reaction is combined with selective hydrogenation of PMI to form THPMI.

In other embodiments, the present invention provides selective dehydrogenation of a saturated carbocyclic compound to form an unsaturated carbocyclic compound as substantially described and shown.

In other embodiments, the present invention provides selective hydrogenation of an aromatic compound to form an unsaturated carbocyclic compound as substantially described and shown.

While not intended to be limiting, the generic structures of the fragrance backbones are used to illustrate application of the technologies disclosed herein in synthesis of compounds useful as fragrances, and the general technology of dehydrogenation is applicable to synthesis of these backbones to introduce double bond(s) into the molecule using various precious and non-precious metal catalyst systems.

The method for dehydrogenation for these substrates can be Standard dehydrogenation using catalysts including but not limited to heterogeneous dehydrogenation catalysts: platinum group metals, combination of metals, supported and non-supported metal catalysts and homogenous catalysts including but not limited to pincer based catalyst systems with or without hydrogen acceptor. The method for dehydrogenation can also be oxidative dehydrogenation using oxygen, air, peroxides and catalysts including but not limited to heterogeneous catalysts such as boric acid, vanadium oxide, molybdenum oxide supported or unsupported and homogeneous catalysts including but not limited to metal complexes with or without solvents and ligand systems. The operating temperatures for dehydrogenations can be from 50 to 800° C. (with a lower limit of 50, 80, 100, 120, 150, or 200° C. and an upper limit of 800, 700, 600, 500, 400, 300, 200, or 150° C.), more preferably in the range of 100-400° C.

The following general synthetic schemes illustrate utility of the dehydrogenation processes to the synthesis of fragrance-related compounds:

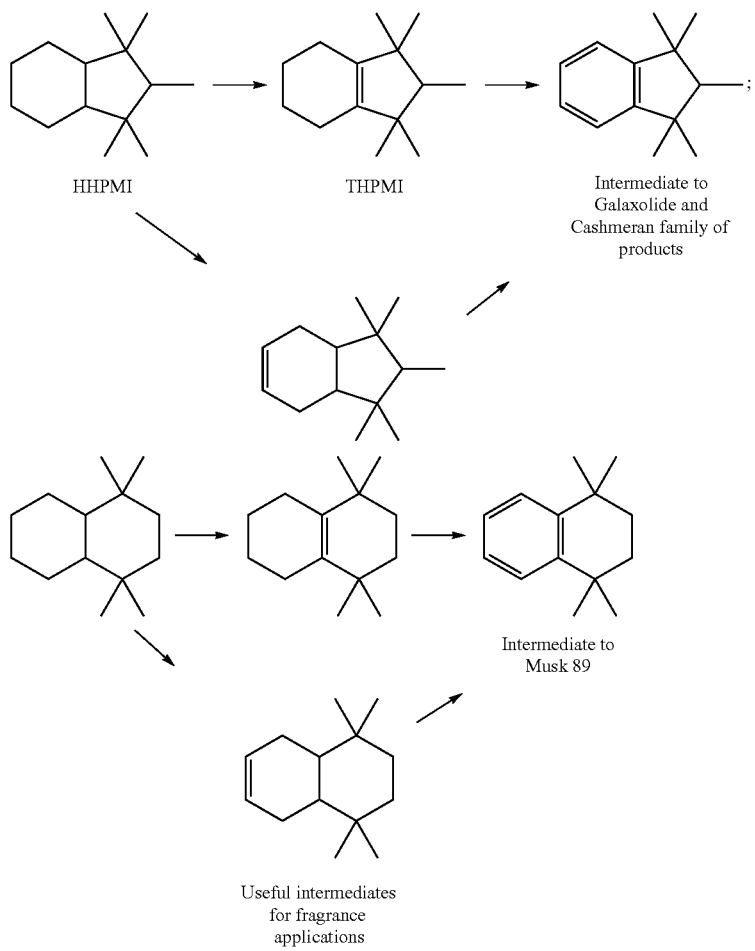

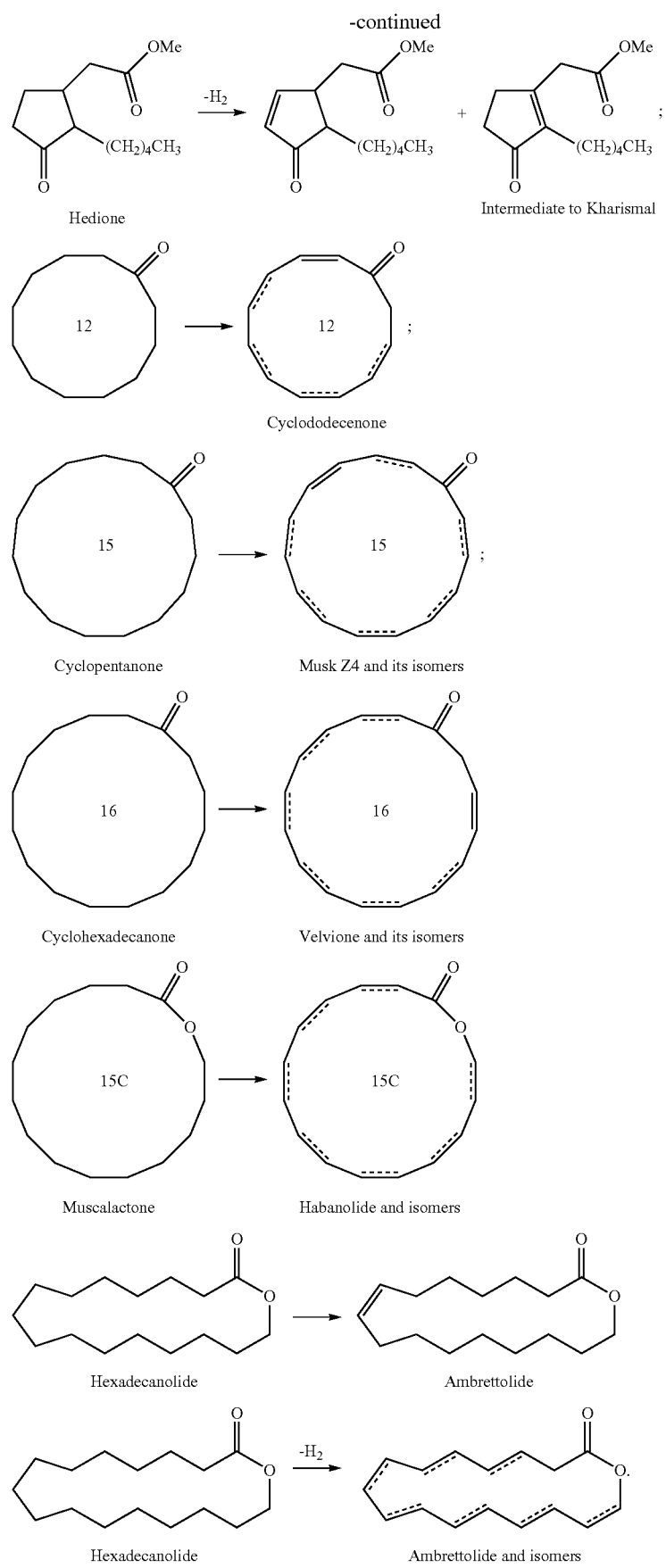

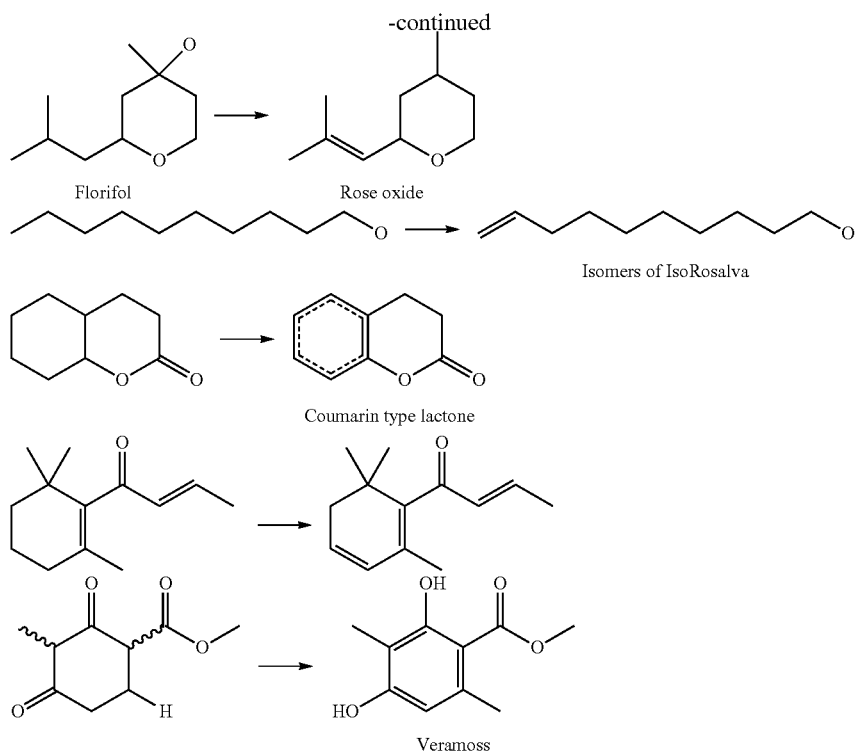

In the above schemes, ⚌ is a single or double bond and at least one ⚌ is a double bond.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The invention is described in greater detail by the following non-limiting examples. Without further elaboration, it is believed that one skilled in the art can, based on the description herein, utilize the present invention to its fullest extent. All publications cited herein are incorporated by reference in their entirety.

Example 1

Dehydrogenation Using Commercial Heterogeneous Catalysts

Two commercially available heterogeneous catalysts 5% Pd/C and 10% Pd/C were used to prepare fragrance ingredients such as galaxolide analogs (e.g., Galaxolide HC, which is 2,3-Dihydro-1,1,2,3,3-Pentamethyl-1H-Indene, hereinafter "PMI") from 1,1,2,3,3-pentamethyloctahydro-1H-indene (HHPMI) at 70% and 100% yields respectively, as demonstrated in the following formula:

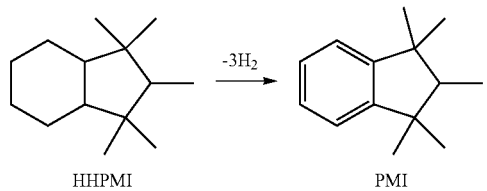

Example 2

Selective Dehydrogenation Using Bi-Metallic Catalyst Formulations

Different compositions of bimetallic catalyst systems were prepared and tested for preparation of THPMI from HHPMI. (Cf. the limited literature precedents: Pt—Sn, Pt—Tl, Pt—Co, Pd—Ag with a selectivity of 25-60% and a very low conversion (<5%). See *Applied Catalysis A*: General Volume 469 (2014), 300-305; *International Journal of hydrogen energy* 37(2012), 6756-63.)

Use of the 5% Pd-1% Ag catalyst on silica support led to 26% selectivity of THPMI at about 10% conversion from HHPMI.

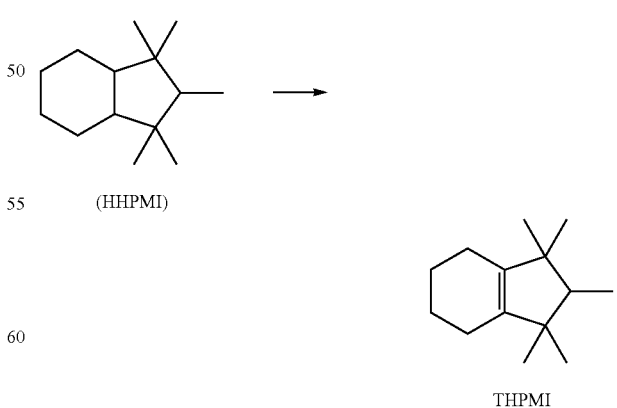

Various combinations and compositions of bi-metallic systems could be prepared and usable in preparing an unsaturated compound including THPMI.

Example 3

Selective Dehydrogenation Using Homogeneous Pincer-Based Catalyst Systems

Suitable homogenous iridium-based pincer catalyst systems include those reported in the publications such as *J. Am. Chem. Soc.* 1997, 119, 840-41; *Chem. Commun.* 1999, 2443-49; *Alkane Dehydrogenation*, In Alkane C—H Activation by Single-Site Metal Catalysis, Pérez, P. J., Ed. Springer: New York, 2012, Vol. 38, Chapter 4; *Chem. Rev.* 2014, 114, 12024-87; and US20150251171A1.

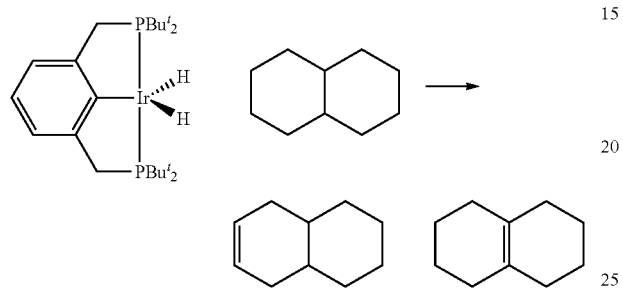

Dehydrogenation using homogeneous pincer based catalyst systems gives high conversions, e.g., 50% or higher, with high selectivity (e.g., 80% or high and 90% or higher) for unsaturated backbones described above and those shown below:

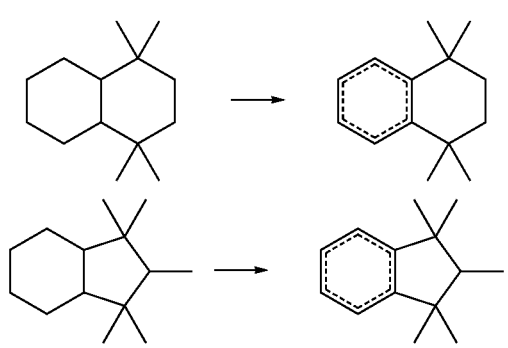

Example 4

Oxidative Dehydrogenation

Oxidative dehydrogenation of cycloalkane to cycloalkene using boric acid involves a 2-step process, oxidation to alcohol and dehydration to cycloalkene.

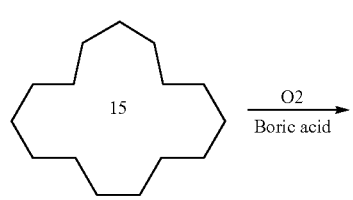

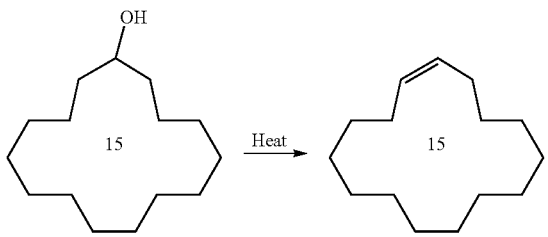

Suitable catalysts include molybdenum oxide, vanadium oxide, magnesium-doped vanadium and molybdenum oxide, and cobalt-doped vanadium phosphorous oxide with or without various oxidants using one step process. Other useful catalysts are described in *J. Cat.* 12, 287-91 (1991); *J. Cat.* 164, 28-35 (1996); *Journal of the Taiwan Institute of Chemical Engineers* (2015) 1-10). As an illustration, oxidative dehydrogenation of cyclohexane to cyclohexene was achieved in 70% selectivity at 40% conversion.

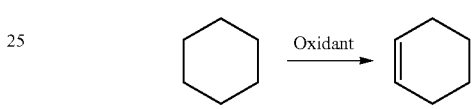

Results from Cyclopentadecane dehydrogenation are shown in Table 1 below:

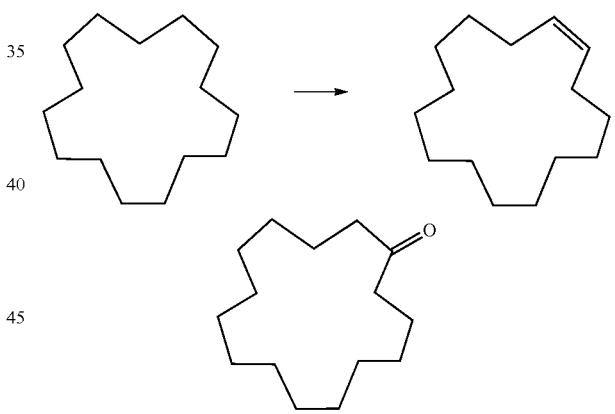

TABLE 1

| Conditions | Catalyst |
|---|---|
| In a batch reactor at 180° C. 800 rpm With Air | Molybdenum Oxide |
| In a flow reactor at 450° C. No Air | Vanadium Oxide Pd/CG |

Example 5

Results on Isolongifolene dehydrogenation using various catalyst systems are shown below:

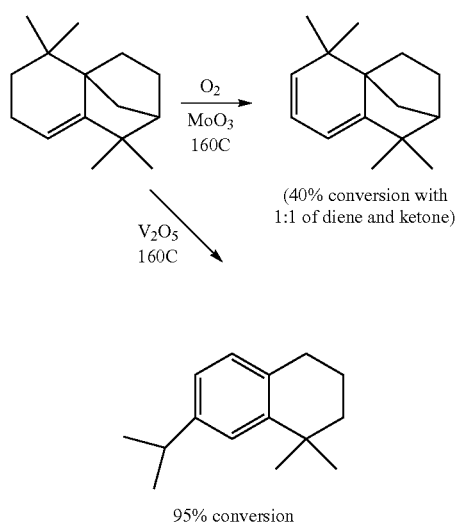

95% conversion

Example 6

Dehydrogenation of ketones or aldehydes can yield the corresponding α,β-unsaturated ketones or aldehydes using the catalysts described above including palladium catalysts, e.g., palladium (II) acetate Pd(OAc)$_2$ and dimethyl sulfoxide (DMSO) coordinated palladium trifluoroacetate Pd(DMSO)$_2$(TFA)$_2$ with oxygen and solvent. See, e.g., S. Stahl et al, Chem. Sci., 2012, 3, 887-891; J. Zhu et al., Adv. Synth. Catal., 2009, 351, 1229; J. Liu et al., Chem.-Asian J., 2009, 4, 1712; and Zhao et al, Chem. Sci., 2012, 3, 883-886.

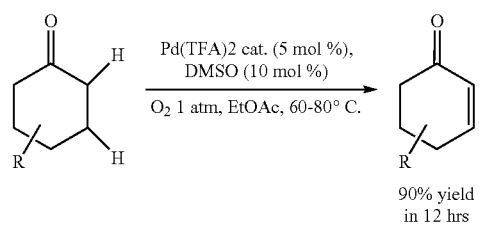

90% yield in 12 hrs

In the scheme above, the reaction is carried out using DMSO coordinated palladium (II) trifluoroacetate Pd(TFA)$_2$ with oxygen (O$_2$) at a pressure of 1 atmosphere in ethyl acetate (EtOAc) at a temperature of 60 to 80° C.

Specific applications to fragrance backbones are shown below.

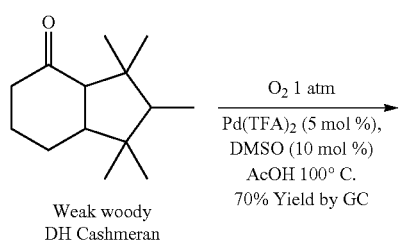

Weak woody
DH Cashmeran

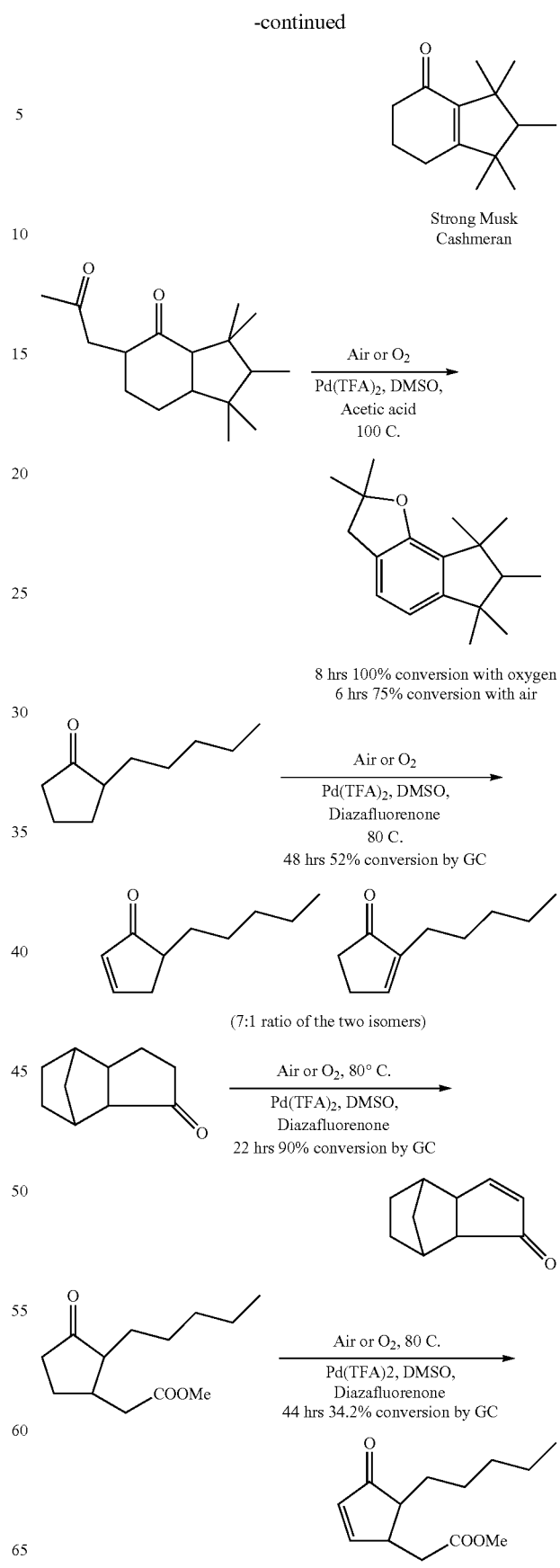

Example 7

Engineering Solution to Enhance Yield of Mono-Unsaturated Alkene Via Combination of Hydrogenation, Dehydrogenation and Separation—THPMI The selective hydrogenation of 1,1,2,3,3-pentamethylindane (PMI) to 1,1,2,3,3-pentamethyl-4,5,6,7-tetrahydro-1H-indene (THPMI) is an intermediate step in the synthesis of Cashmeran family of products. A significant amount of over-hydrogenated by-product is formed in known processes.

A process of this invention is a breakthrough to this long standing problem in the known processes. This process utilizes a combination of hydrogenation and dehydrogenation steps in converting the waste stream to the starting material (PMI) and then converting PMI to THPMI in a continuous fashion, e.g., in a flow reactor. The combination of selective hydrogenation and dehydrogenation in flow reactors turn the waste stream to the useful intermediates or products in a continuous reactor, e.g., a flow reactor, thus improving the overall yield.

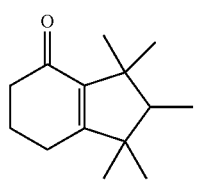

Cashmeran 6,7-dihydro-1,1,2,3,3-pentamethyl-4(5H)-indanone

THPMI is prepared following these steps: (a) feeding PMI into a first flow reactor having a fixed bed catalyst; (b) hydrogenating PMI in the first flow reactor to produce a product mixture; (c) separating HHPMI from the product mixture in a first separation column to obtain a first side stream containing the by-product HHPMI and a main stream containing THPMI; (d) passing the first side stream into a second flow reactor having a second fixed bed catalyst; (e) dehydrogenating HHPMI to PMI in the second flow reactor to obtain a dehydrogenation stream; (f) feeding the dehydrogenation stream into the first flow reactor; (f) separating the main stream in a second separation column to obtain a second side stream containing PMI and a product stream containing THPMI with a purity of 85% or greater; (g) feeding the second side stream into the first flow reactor; and (h) collecting the product stream containing THPMI.

The first fixed bed catalyst provides a high selectivity for preparing THPMI. Any catalysts described above can be used as the first fixed bed catalyst.

This process of the invention can have a continuous 2-column separation of THPMI from the reaction mixture with a high efficiency and a high purity, e.g., at 85% or greater, and at the same time, recovering the by-product HHPMI and the unreacted starting material PMI in a separate side stream. PMI is then fed into the first flow reactor, i.e., the hydrogenation flow reactor, to be converted to THPMI. HHPMI is fed into the second flow reactor, i.e., the dehydrogenation reactor, to be converted to PMI, which is in turn fed into the first flow reactor for conversion to THPMI.

This process scheme is depicted in FIG. 1 and described in greater detail below.

Flow Hydrogenation of PMI

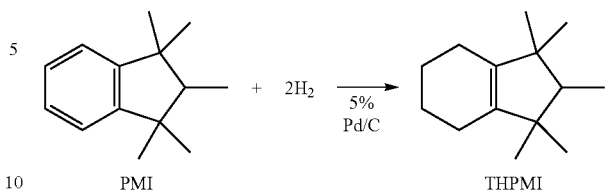

PMI is allowed to pass through the first flow reactor containing the first fixed bed catalyst. In the first flow reactor, PMI is selectively hydrogenated to the desired product THPMI. The reaction is highly exothermic and preferred carried out at a high pressure (e.g., >500 psi and 600 to 1200 psi) in the flow reactor and a temperature of 165-185° C. for good selectivity of THPMI. Major by-product obtained from the reaction is HHPMI from over hydrogenation of THPMI as shown in the side reaction below. Some unreacted PMI is also present for typical process conditions.

Side Reaction

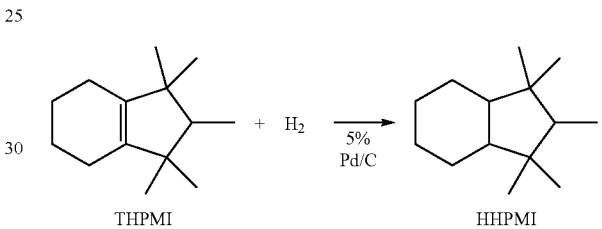

Catalysts for Hydrogenation

Several fixed bed catalysts were used in the hydrogenation of PMI to THPMI. The results are shown in the Table 2 below. Combining this process with continuous separation and dehydrogenation of waste streams (described in following sections) has proved to prepare THPMI in a high overall yield. The overall yield is calculated as: the actual yield of THPMI by weight/the theoretical yield of THPMI based on the initial PMI fed into the flow reactor×100%.

TABLE 2

Hydrogenation results using different types of fixed bed 5% Pd/C catalysts

| Catalyst | Avg. Pressure (psi) | Gas flow-rate (sccm) | Liquid flow-rate (ml/min) | T (° C.) | THPMI Conc. (%) | Conversion PMI (%) | Selectivity (%) |
|---|---|---|---|---|---|---|---|
| Catalyst A | 700 | 60 | 0.2 | 180 | 44.6 | 66.7 | 67 |
| Catalyst B | 700 | 30 | 0.15 | 175 | 18.8 | 50.7 | 37 |
| Catalyst C | 700 | 60 | 0.12 | 170 | 47.4 | 60.6 | 78 |
| Catalyst D | 700 | 25 | 0.17 | 165 | 43.2 | 59 | 74 |

Avg. Pressure is calculated as (the pressure in the inlet of the flow reactor+the pressure in the outlet of the flow reactor)/2.

The gas flow rate refers to the flow rate of hydrogen gas fed into the flow reactor measured at 1 atmosphere and 0° C. It is measured in sccm units, i.e., Standard Cubic Centimeters per Minute, indicating $cm^3$/min at a standard temperature and pressure (i.e., 1 atmosphere and 0° C.). The standard temperature and pressure vary according to different regulatory bodies.

The liquid flow rate is the flow rate of PMI fed into the flow reactor.

THPMI is the concentration of THMPI in the stream coming out of the flow reactor.

Conversion PMI is the moles of PMI consumed/the moles of PMI fed into the flow reactor.

The selectivity is calculated as the moles of THPMI/the total moles of PMI consumed.

Continuous Separation of Product Stream Containing THPMI

The product stream from the hydrogenation contains the desired product THPMI, the by-product HHPMI, and the unreacted PMI. THPMI is separated from the product stream using two separate columns, together having a high efficiency of 40-50 stage separation. After the separation, THPMI is obtained at a purity of 85%. HHPMI is easily separated from THPMI and PMI using a separation column, leaving a mixture of THPMI and PMI, which requires a separation column with a very high efficiency.

Flow Dehydrogenation of HHPMI to PMI

The separated HHPMI constitutes about 20 to 25% of the product stream. It is then dehydrogenated to PMI in a second flow reactor. The newly generated PMI is allowed to pass through the first flow reactor again to be converted to THPMI.

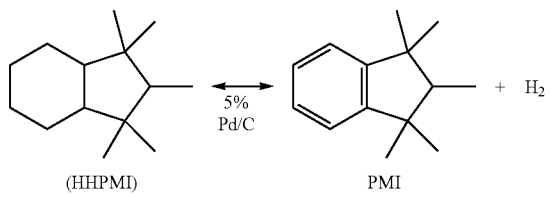

(HHPMI)                    PMI

The reaction is an equilibrium limited process and in order to drive the process to the desired product, hydrogen must be removed from the process. Nitrogen is typically used to purge the liberated hydrogen from the system. The reaction is highly endothermic and requires high operating temperatures and high catalyst loading.

Catalysts for Dehydrogenation

Catalysts suitable for dehydrogenation of HHPMI include Pd/C and Pt/C. The dehydrogenation results are shown in Table 2 below. The results show ~70% conversion of HHPMI to PMI with these two catalysts.

TABLE 3

Dehydrogenation results in the second flow reactor using different types of 5% Pd/C

| Catalyst Entry# | Nitrogen flowrate (sccm) | Liquid flowrate (ml/min) | T (° C.) | Conv. of HHPMI to PMI (%) |
|---|---|---|---|---|
| Catalyst C | 10 | 0.03 | 340 | 69.12 |
| Catalyst D | 10 | 0.05 | 300 | 70.06 |

Process Scheme

Based on the results from continuous hydrogenation, distillation and dehydrogenation, a new process scheme proposed to obtain 85% THPMI yield at low cost is illustrated in FIG. 1.

Experimental Setup for Hydrogenation of PMI

The liquid reactant was pumped using the HPLC pump which can deliver liquid in the flowrate range from 0 to 10 ml/min. The hydrogen gas flows through the Mass Flow Controller (MFC) at the desired flowrate and mixed with the liquid stream using a micromixer. The combined gas-liquid mixture then entered the fixed bed reactor which was immersed in a constant temperature oil bath (or heated using electric furnace). Frits made of SS316L, with 2 microns opening were connected to the ends of the reactor to prevent the catalyst from moving out of the reactor. From the reactor, the reaction mixture was passed through the back pressure regulator. From the back pressure regulator, the mixture was passed to a product receiver where the liquid was collected in a glass vessel and the gas phase is vented to the atmosphere.

Experimental Setup for Dehydrogenation of PMI

The liquid reactant is pumped using the HPLC pump which can deliver liquid in the flowrate range from 0 to 10 mL/min. Compressed nitrogen flows through the Mass Flow Controller (MFC) at the desired flow and mixed with the liquid stream using a micromixer. The combined gas-liquid mixture then enters the fixed bed reactor containing the catalyst which is heated using an electric furnace. From the reactor, the reaction mixture is cooled using a cooling bath and then the product mixture is collected in a receiver.

The foregoing examples or preferred embodiments are provided for illustration purpose and are not intended to limit the present invention. Numerous variations and combinations of the features set forth above can be utilized without departing from the present invention as set forth in the claims.

What is claimed is:

1. A method of preparing an unsaturated compound, comprising dehydrogenation of a corresponding saturated compound in the presence of a catalyst system under conditions that effect loss of one or more molecules of hydrogen ($H_2$) per molecule of the saturated compound, wherein the catalyst system is a heterogeneous catalyst system selected from the group consisting of Pd/C, Pd/alumina, Pd/silica, Pd/CG, Pt/C, Pt/alumina, molybdenum oxide, vanadium pentoxide, Rh/alumina, Ru/$Al_2O_3$, bismuth molybdate, and combinations thereof;

the saturated compound is selected from the group consisting of:

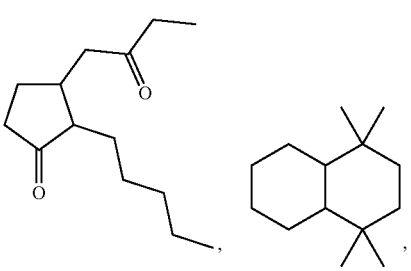

-continued
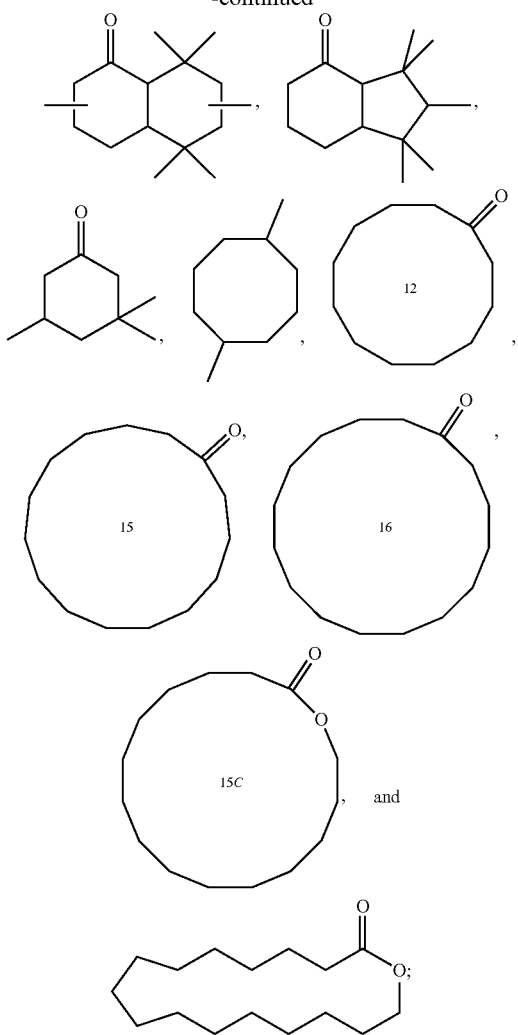
and
the unsaturated compound is
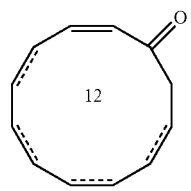
when the saturated compound is
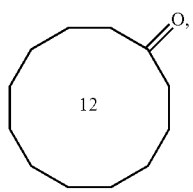 [SMILES: O=C1CCCCCCCCCCC1]
the unsaturated compound is
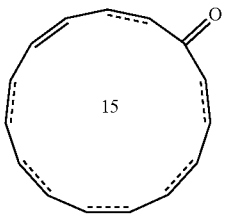
when the saturated compound is
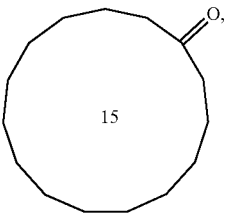 [SMILES: O=C1CCCCCCCCCCCCCC1]
the unsaturated compound is
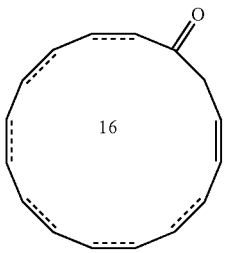
when the saturated compound is
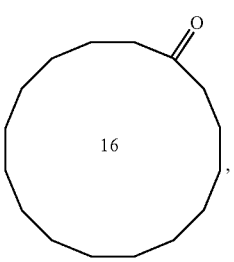 [SMILES: O=C1CCCCCCCCCCCCCCC1]
the unsaturated compound is
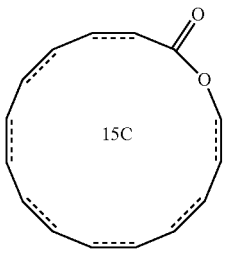

when the saturated compound is

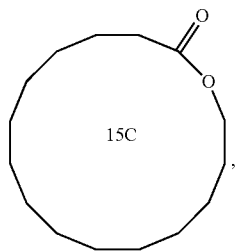

and the unsaturated compound is

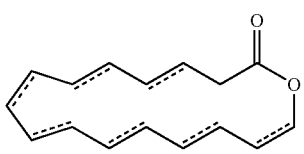

when the saturated compound is

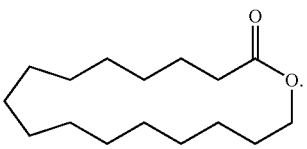 [SMILES: O=C1CCCCCCCCCCCCCCCO1]

2. The method of claim 1, wherein said conditions comprise one or more solvents, an elevated temperature, and/or a stream of nitrogen to purge liberated hydrogen.

3. The method of claim 1, further comprising adding one or more hydrogen acceptors to the dehydrogenation reaction to consume the hydrogen molecules.

4. The method of claim 1, wherein dehydrogenation is performed in a flow reactor in the presence of a fixed-bed catalyst.

5. The method of claim 4, wherein said fixed-bed catalyst is selected from the group consisting of Pd/C, Pd/alumina, Pd/Silica, Pd/CG, Pt/C, Pt/alumina, molybdenum oxide, vanadium pentoxide, Rh/alumina, Ru/Al$_2$O$_3$, and bismuth molybdate, and combinations thereof.

* * * * *